United States Patent [19]

Inoue et al.

[11] Patent Number: 4,897,406
[45] Date of Patent: Jan. 30, 1990

[54] RHODANINE DERIVATIVES AND PHARMACEUTICAL COMPOSITIONS

[75] Inventors: Hitoshi Inoue; Hiroyasu Koyama; Reiko Kubota; Hirohiko Komatsu, all of Saitama, Japan

[73] Assignee: Nisshin Flour Milling Co., Ltd., Japan

[21] Appl. No.: 269,776

[22] Filed: Nov. 9, 1988

[30] Foreign Application Priority Data

Nov. 13, 1987 [JP] Japan .................. 62-288998

[51] Int. Cl.$^4$ .................. C07D 277/34; A01K 31/425
[52] U.S. Cl. .................. 514/369; 548/183
[58] Field of Search .................. 548/183; 514/369

[56] References Cited

U.S. PATENT DOCUMENTS

| | | | |
|---|---|---|---|
| 3,678,041 | 7/1972 | Mousseron | 548/183 |
| 4,703,052 | 10/1987 | Eggler | 548/183 |
| 4,714,765 | 12/1987 | Ogawa et al. | 548/183 |
| 4,777,259 | 10/1988 | Ogawa | 548/183 |
| 4,791,126 | 12/1988 | Tanouchi | 548/183 |

FOREIGN PATENT DOCUMENTS 211670 8/1986 European Pat. Off. .......... 548/183
29570 2/1987 Japan .................. 548/183

*Primary Examiner*—Robert Gerstl
*Attorney, Agent, or Firm*—Abelman Frayne Rezac & Schwab

[57] ABSTRACT

Disclosed are a compound of the formula

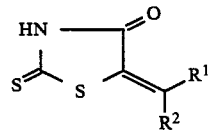

wherein $R^1$ is $C_1$–$C_6$ alkyl or a group —$(CH_2)_n COOR^3$ in which n is an integer of 1 to 4 and $R^3$ is hydrogen or $C_1$–$C_6$ alkyl, and $R^2$ is a group —CH=CH—$R^4$ or —$CH_2$—$CH_2$—$R^4$ in which $R^4$ is substituted or unsubstituted phenyl or a substituted or unsubstituted 5-membered heterocyclic group, or a pharmaceutically acceptable salt thereof, and a pharmaceutical composition comprising the same as an active ingredient. The compounds have an excellent chemical mediator inhibitory activity.

2 Claims, No Drawings

RHODANINE DERIVATIVES AND PHARMACEUTICAL COMPOSITIONS

FIELD OF THE INVENTION

The present invention relates to new rhodanine derivatives, processes for their preparation and pharmaceutical compositions having a chemical mediator inhibitory activity which comprises said rhodanine derivatives as active ingredients.

BACKGROUND OF THE INVENTION

For treatment of asthma, there has been hitherto applied multiple treatments such as treatment with drugs, treatment by change of air, treatment by desensitization, psychological treatment, etc., but there has not yet been established a method to accomplish a satisfactory therapeutic effect.

The drugs which have been nowadays utilized conventionally as an antiasthmatic drug include a $\beta$-receptor-stimulating agent, a xanthine agent, a steroidal agent, an antihistaminic agent, an inhibitor of chemical mediator and the like. However, it is the present status that such various antiasthmatic agents have both merits and demerits, respectively, and all of them could not accomplish a satisfactory therapeutic effect.

Pathophysiology of asthma has not yet been completely elucidated and it is believed that its occurrence would arise from final reflection from complex pathologic conditions. Thus, the drug which could show multiple pharmacological actions rather than a sole action would be preferable as an antiasthmatic drug.

Recently, it has been elucidated and given attention that SRS-A, i.e. Slow Reacting Substance of Anaphylaxis, which has been known for a long time to be one of important chemical mediators for immediate anaphylaxis or asthma, is a metabolite of arachidonic acid by 5-lipoxygenase pathway, that is a mixture of luekotrienes $C_4$, $D_4$ and $E_4$. Leukotrienes are considered to be a potent chemical mediator for allergic or inflammatory reactions and cause such disorders as contracts of smooth muscles, e.g. bronchial muscle or pulmonary blood vessels, or increased vascular permeability and the like. Further, it has been elucidated that they could show such actions as promotion of mucosus secretion, decrease in ciliary movement, contraction of coronary blood vessel and so on.

Moreover, it has been suggested that histamines, leukotriene $B_4$, PAF of prostaglandins, e.g. $PGF_{2x}$, $PGD_2$, $TXA_2$, in addition to SRS-A, could participate in allergy or inflammation.

DISCLOSURE OF INVENTION

In accordance with the invention, we have found that rhodanine derivatives of formula (I) are of a potent inhibitory activity against chemical mediators including leukotrienes.

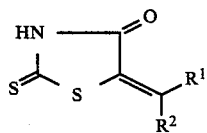
(I)

wherein $R^1$ is $C_1$-$C_6$ alkyl or a group $-(CH_2)_nCOOR^3$ in which n is an integer of 1 to 4 and $R^3$ is hydrogen or $C_1$-$C_6$ alkyl, and $R^2$ is a group $-CH=CH-R^4$ or $-CH_2-CH_2-R^4$ in which $R^4$ is substituted or unsubstituted phenyl or a substituted or unsubstituted 5-membered heterocyclic group, and a pharmaceutically acceptable salt thereof.

According to a further aspect of the present invention, there is provided a pharmaceutical composition which comprises as an active ingredient a rhodanine derivative of formula (I) as defined above, or a pharmaceutically acceptable salt thereof, associated with one or more pharmaceutically acceptable additives or excipients therefor.

Examples of $C_1$-$C_6$ alkyl groups represented by $R^1$ and $R^3$ in the formula (I) are straight chain or branched chain $C_1$-$C_6$ alkyl groups such as methyl, ethyl, n-propyl, isopropyl, butyl, sec-butyl, tert-butyl, iso-butyl, pentyl, sec-pentyl, hexyl, etc. Specific examples of $R^1$ are methyl, ethyl, n-propyl, isopropyl, hexyl, $-(CH_2)_3COOH$, $-(CH_2)_3COOCH_3$, $-CH_2CH_2COOC_2H_5$, etc.

Examples of the substituents for phenyl represented by $R^4$ include $C_1$-$C_6$ alkyl, $C_1$-$C_6$ alkoxy, hydroxyl, halogen, carboxyl and carboxyl-, alkoxycarbonyl- or tetrazolyl-substituted alkoxy, etc.

The 5-membered heterocyclic groups of $R^4$ include those containing in its ring structure N or S as the heteroatom, such as thienyl, pyrrolyl, etc. The substituents for the heterocyclic group include halogen, etc.

The rhodanine derivatives of formula (I) may exist in various isomeric forms, because of $R^1$ and $R^2$ being present at the 5-position through a double bond and depending on the definitions of $R^1$ and $R^2$. The present invention is not limited to any particular isomer but includes all possible individual isomers and racemates.

Where the rhodanine derivatives of formula (I) have an acid group in the compound, they can form the salts with pharmaceutically acceptable bases. The present invention also includes the pharmaceutically acceptable salts thus formed.

Illustrative examples of the compounds of formula (I) are listed below.
5-($\alpha$-Methyl-3,4-dimethoxycinnamylidene)-4-oxo-2-thioxothiazolidine,
5-($\alpha$-Methyl-4-methylcinnamylidene)-4-oxo-2-thioxothiazolidine,
5-($\alpha$-Methyl-4-methoxycinnamylidene)-4-oxo-2-thioxothiazolidine,
5-($\alpha$-Methyl-3,5-di-tert-butyl-4-hydroxycinnamylidene)-4-oxo-2-thioxothiazolidine,
5-($\alpha$-Methyl-3,4,5-trimethoxycinnamylidene)-4-oxo-2-thioxothiazolidine,
5-($\alpha$-Methyl-4-chlorocinnamylidene)-4-oxo-2-thioxothiazolidine,
5-($\alpha$-Methyl-3,4,-dichlorocinnamylidene)-4-oxo-2-thioxothiazolidine,
5-($\alpha$-Propyl-3,4-dimethoxycinnamylidene)-4-oxo-2-thioxothiazolidine,
5-($\alpha$-Propyl-3,4,5-trimethoxycinnamylidene)-4-oxo-2-thioxothiazolidine,
5-[3-(2-Thienyl)-1-ethyl-2-propenylidene]-4-oxo-2-thioxothiazolidine,
5-[3-(2-Pyrrolyl)-1-methyl-2-propenylidene]-4-oxo-2-thioxothiazolidine,
5-[3-(3,4-Dimethoxyphenyl)-1-methylpropylidene]-4-oxo-2-thioxothiazolidine,
Ethyl 4-[3-(4-oxo-2-thioxo-5-thiazolidinylidene)-1-buten-1-yl]phenoxyacetate,
Ethyl 6-(3,4-dimethoxyphenyl)-4-(4-oxo-2-thioxo-5-thiazolidinylidene)-5-hexanoate, 5-[3-(2-Thienyl)-1-methyl-2-propenylidene]-4-oxo-2-thioxothiazolidine, 5-[3-(5-Chloro-2-thienyl)-1-methyl-2-propenylidene]-4-oxo-2-thioxothiazolidine, 4-[3-(4-Oxo-2-thioxo-5-thiazolidinylidene)-1-hexen-1-yl]benzoic acid, 4-[3-(4-Oxo-2-thioxo-5-thiazolidinylidene)-1-buten-1-yl]phenoxyacetic acid, 7-(3,4,-Dimethoxyphenyl)-5-(4-oxo-2-thioxo-5-thiazolidinylidene)-6-heptenoic acid, and 5-[α-Hexyl-4-(1H-tetrazol-5-yl)methoxycinnamylidene]-4-oxo-2-thioxothiazolidene.

The compounds of formula (I) can be prepared by reacting rhodanine of formula (II)

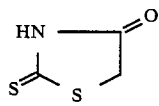

with a ketone of formula (III)

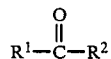

wherein $R^1$ and $R^2$ have the same meaning as defined above.

In this reaction, the ketone of formula (III) may be employed in the range of 0.5 to 10 moles per mole of rhodanine of formula (II), but both may be usually employed in equimolar amounts. The ketones are preferably used in a slightly excess amount relative to rhodanine, e.g. 1.1 to 1.5 moles of the ketones per mole of rhodanine of formula (II).

This reaction may be carried out in the absence of an organic solvent. The organic solvents used include hydrocarbons such as n-hexane, ligroin, benzene, toluene, etc.; lower alcohols such as methanol, ethanol, isopropanol, etc.; ether solvents such as ether, tetrahydrofuran, dioxane, etc.; esters such as ethyl acetate, butyl acetate, etc.; chlorinated hydrocarbons such as ethylene dichloride, chloroform, trichloroethylene, carbon tetrachloride, etc.,; aprotic polar solvents such as dimethyl sulfoxide, dimethylformamide, diethylformamide, dimethylacetamide, etc.; and protic polar solvents such as formic acid, acetic acid, etc., and such solvents may be employed alone or in admixture with two or more thereof.

The reaction may be carried out at any temperature and preferably under heating. Generally, the reaction may be carried out at a temperature of 50° to 150° C., depending upon the solvents to be employed. Further, the reaction is preferably conducted at a temperature in the neighborhood of the boiling point of the solvent employed, which is easily controllable for the reaction temperature.

Preferably, a catalyst may be added for promoting the reaction. The catalysts used include ammonia; secondary amines such as piperidine, diethylamine, etc.; salts of organic acids such as ammonium acetate, sodium acetate, etc. Such catalysts may be employed alone or in combination with two or more thereof. These catalysts may be used in the range of 0.2 to 5 moles per mole of rhodanine of formula (II), with the range of 1.0 to 1.5 moles being preferred.

The reaction will be completed in 1 to 12 hours, depending upon the reactivity of reactants employed and such conditions as reaction temperature, etc.

The reaction product may be separated from the reaction mixture obtained as above according to any conventional means in this art. For instance, the reaction product can be isolated by such means as concentration of the reaction mixture followed by separation by recrystallization or separation by chromatography, etc.

The rhodanine derivatives of formula (I), when having the acid group therein, can be converted into the pharmaceutically acceptable salts in a conventional manner. Examples of the bases used for the formation of the salts are hydroxides or carbonates of alkali metals such as sodium, potassium, etc. or alkaline earth metals such as magnesium, calcium, etc.; aluminum hydroxide; ammonia; ammonium carbonate; primary amines such as methylamine, ethylamine, etc.; secondary amines such as diethylamine, morpholine, etc,; and tertiary amines such as triethylamine, pyridine, etc.

The compounds of formula (I) and pharmaceutically acceptable salts thereof have an inhibitory activity on leukotrienes and an inhibitory activity on biosynthesis and release of chemical mediators. Thus, they are extremely useful against all allergic diseases including bronchial asthma, ischemic heart diseases, arteriosclerosis, psoriasis, inflammations, etc.

The pharmaceutical composition of the invention may be administered orally or parenterally in the form of usual pharmaceutical preparations. Pharmaceutical preparations may include tablets, capsules, suppositories, troches, syrups, creams, ointments, plasters, cataplasms, granules, powders, injections, suspensions, inhalations, aerosols and the like. They may be formed into double layer tablets or multilayer tablets with other drugs. Further, tablets may be formed, if necessary, into tablets having usual coated films, e.g. sugar-coated tablets, enteric-coated tablets, film-coated tablets.

For the formulation of solid preparations, suitable additives are employed such as lactose, refined sugar, crystalline cellulose, corn starch, calcium phosphate, sorbitol, carboxymethylcellulose, gum arabic, polyvinylpyrrolidone, hydroxypropylcellulose, glycerol, polyethylene glycol, stearic acid, magnesium stearate, talc, etc.

For the formulation of semi-solid preparations, there may be used vegetable or synthetic waxes or fats, etc.

For the formulation of liquid preparations, suitable additives may be used such as sodium chloride, sorbitol, glycerol, olive oil, almond oil, propylene glycol, ethyl alcohol, etc. The formulations may additionally include lubricating agents, wetting agents, emulsifying and suspending agents, preserving agents, sweetening agents or flavoring agents.

The pharmaceutical preparations may contain 0.1 to 100% by weight of the active ingredient and, suitably, 1 to 50% by weight for oral administration and 0.1 to 10% by weight for injection.

The active compounds are effective over a wide dosage range. For example, dosages per day will normally fall within the range of 0.01 to 1000 mg/kg of body weight, but the amount of the compound actually administered will be determined by a physician in the light of the relevant circumstances including the condition to be treated, the chosen route of administration, the age, sex distinction, the severity of the patient's symptoms, etc. The above dosage ranges are not intended to limit the scope of the invention.

This invention will be more fully explained by way of the following examples not limiting the scope of this invention.

EXAMPLE 1

5-(α-Methyl-3,4-dimethoxycinnamylidene)-4-oxo-2-thioxothiazolidine

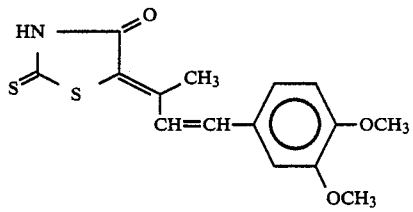

A mixture of 1.73 g (0.013 mol) of rhodanine, 2.06 g (0.01 mol) of 3,4-dimethoxybenzalacetone, 0.31 g (0.004 mol) of ammonium acetate and 5 ml of toluene was heated under reflux for 2 hours. After cooling, precipitates were recovered by filtration and washed with methanol. The residue was purified by silica gel column chromatography (eluent, chloroform) to obtain 0.5 g of the isomer A of the desired 5-(α-methyl-3,4-dimethoxycinnamylidene)-4-oxo-2-thioxothiazolidine from the first eluate and 0.2 g of the isomer B from the subsequent eluate.

Isomer A

Orange crystals, m.p. 244°-246° C. (dec.).
Mass spectrum (m/e); 321 (M+).
NMR(DMSO-$d_6$) δ(ppm): 2.15(s, 3H), 3.80(s, 6H), 6.97-7.20(m, 3H), 7.27(d, 1H, J=16 Hz), 8.30(s, 1H), 8.40(d, 1H, J=16 Hz).
IR(KBr) $cm^{-1}$: 1665, 1600, 1510, 965.

Isomer B

Red crystals, m.p. 239°-241° C. (dec.).
Mass spectrum (m/e); 321 (M+).
NMR(DMSO-$d_6$) δ(ppm): 2.53(s, 3H), 3.80(s, 3H), 3.82(s, 3H), 6.65(d, 1H, J=16 Hz), 6.85-7.40(m, 4H).
IR(Nujol) $cm^{-1}$: 1670, 1660, 1600, 960.

EXAMPLE 2

5-(α-Methyl-4-methylcinnamylidene)-4-oxo-2-thioxothiazolidine

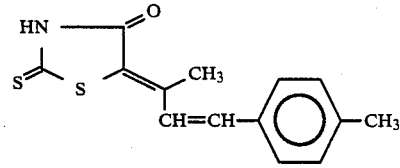

Following the same procedure as in Example 1 but substituting 4-methylbenzalacetone for 3,4-dimethoxybenzalactone, there were obtained 0.4 g of the isomer A and 0.2 g of the isomer B of 5-(α-methyl-4-methylcinnamylidene)-4-oxo-2-thioxothiazolidine.

Isomer A

Yellow crystals, m.p. 251°-254° C. (dec.).
NMR(DMSO-$d_6$) δ(ppm): 2.16(s, 3H), 2.30(s, 3H), 7.20-7.52(m, 5H), 8.50(d, 1H, J=16 Hz).
IR(Nujol) $cm^{-1}$: 1680, 1600, 1550, 980.

Isomer B

Yellow crystals, m.p. 233°-235° C. (dec.).
NMR(DMSO-$d_6$) δ(ppm): 2.32(s, 3H), 2.50(s, 3H), 6.70(d, 1H, J=16 Hz), 7.20(d, 2H, J=8.8 Hz), 7.32(d, 1H, J=16 Hz), 7.58(d, 2H, J=8.8 Hz).
IR(Nujol) $cm^{-1}$: 1680, 1600, 1550, 960.

EXAMPLE 3

5-(α-Methyl-3,5-di-t-butyl-4-hydroxycinnamylidene)-4-oxo-2-thioxothiazolidine

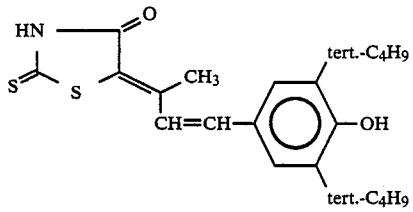

A mixture of 1.20 g (0.009 mol) of rhodanine, 1.64 g (0.006 mol) of 3,5-di-t-butyl-4-hydroxybenzalacetone, 0.23 g (0.003 mol) of ammonium acetate and 5 of toluene was heated under reflux for 7 hours. After cooling, the precipitated crystals were recovered by filtration, washed with water and further methanol to give 0.18 g of the desired 5-(α-methyl-3,5-di-t-butyl-4-hydroxycinnamylidene)-4-oxo-2-thioxothiazolidine.

Reddish brown crystals, m.p. 267°-270° C. (dec.).
Mass spectrum (m/e); 389 (M+).
NMR(CDCl$_3$) δ(ppm): 1.45(s, 18H), 2.60(s, 3H), 5.58(s, 1H), 6.58(d, 1H, J=16 Hz), 7.18(d, 1H, J=16 Hz), 7.35(s, 2H).
IR(Nujol) $cm^{-1}$: 3450, 1680, 1610, 960.

EXAMPLE 4

5-(α-Methyl-4-methoxycinnamylidene)-4-oxo-2-thioxothiazolidine

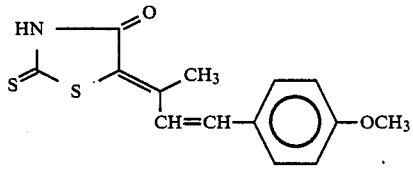

Following the same procedure as in Example 3 but substituting 4-methoxybenzalacetone for 3,5-di-t-butyl-4-hydroxybenzalacetone, there was obtained 0.2 g of the desired 5-(α-methyl-4-methoxycinnamylidene)-4-oxo-2-thioxothiazolidine.

Yellowish brown crystals, m.p. 222°-224° C. (dec.).
Mass spectrum (m/e); 291 (M+).
NMR(DMSO-$d_6$) δ(ppm): 2.15(s, 3H), 3.80(s, 3H), 6.98(d, 2H, J=8 Hz), 7.26(d, 1H, J=16 Hz), 7.54(d, 2H, J=8 Hz), 8.42(d, 1H, J=16 Hz).
IR(Nujol) $cm^{-1}$: 1670, 1600, 1550, 970.

EXAMPLE 5

5-(α-Methyl-3,4,5-trimethoxycinnamylidene)-4-oxo-2-thioxothiazolidine

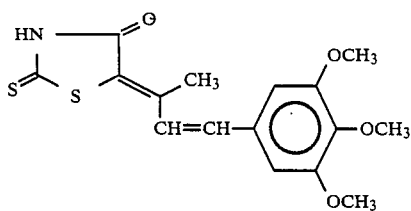

Following the same procedure as in Example 3 but substituting 3,4,5-trimethoxybenzalacetone for 3,5-di-t-butyl-4-hydroxybenzalacetone, there was obtained 0.4 g of the desired 5-(α-methyl-3,4,5-trimethoxycinnamylidene)-4-oxo-2-thioxothiazolidine.

Orange powders, m.p. 270°–274° C. (dec.).
Mass spectrum (m/e); 351 (M+).
NMR(DMSO-$d_6$) δ(ppm): 2.50(s, 3H), 3.70(s, 3H), 3.85(s, 6H), 6.73(d, 1H, J=16 Hz), 7.00(s, 2H), 7.32(d, 1H, J=16 Hz).
IR(Nujol) cm$^{-1}$: 1690, 1610, 1580, 1550, 950.

EXAMPLE 6

5-(α-Methyl-4-chlorocinnamylidene)-4-oxo-2-thioxothiazolidine

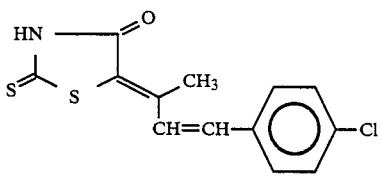

A mixture of 1.33 g (0.01 mol) of rhodanine, 1.80 g (0.01 mol) of 4-chlorobenzalacetone, 20 ml of ethanol and 2 ml of aqueous ammonia was heated under reflux for 4 hours. After cooling, the precipitated crystals were recovered by filtration and washed with methanol to give 0.52 g of the desired 5-(α-methyl-4-chlorocinnamylidene)-4-oxo-2-thioxothiazolidine.

Orange crystals, m.p. 247°–249° C. (dec.).
NMR(DMSO-$d_6$) δ(ppm): 2.16(s, 3H), 7.32(d, 1H, J=16 Hz), 7.48(d, 2H, J=8 Hz), 7.60(d, 2H, J=8 Hz), 8.52(d, 1H, J=16 Hz).
IR(Nujol) cm$^{-1}$: 1675, 1605, 980.

EXAMPLE 7

5-(α-Methyl-3,4-dichlorocinnamylidene)-4-oxo-2-thioxothiazolidine

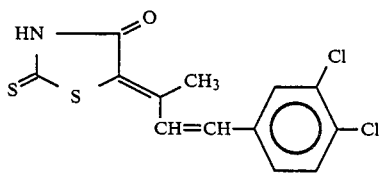

Following the same procedure as in Example 6 but substituting 3,4-dichlorobenzalacetone for 4-chlorobenzalacetone, there was obtained 0.23 g of the title compound.

Yellow crystals, m.p. 242°–245° C. (dec.).
NMR(DMSO-$d_6$) δ(ppm): 2.15(s, 3H), 7.28(d, 1H, J=16 Hz), 7.55(d, 1H, J=8 Hz), 7.67(d, 1H, J=8 Hz), 7.75(s, 1H), 8.50(d, 1H, J=16 Hz).
IR(Nujol) cm$^{-1}$: 1680, 1610, 1555, 975.

EXAMPLE 8

5-(α-Propyl-3,4-dimethoxycinnamylidene)-4-oxo-2-thioxothiazolidine

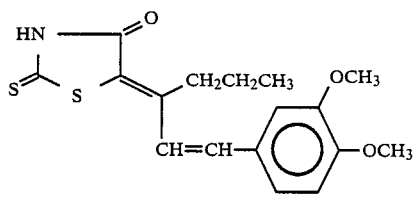

A mixture of 1.46 g (0.011 mol) of rhodanine, 2.34 g (0.01 mol) of 1-(3,4-dimethoxyphenyl)-1-hexen-3-one, 0.77 g (0.01 mol) of ammonium acetate and 20 ml of toluene was heated under reflux for 8 hours. After cooling, 100 of water were added to the reaction mixture, and the layers were then extracted with chloroform (80 ml×3). A chloroform layer was washed twice with water and once with a saturated aqueous solution of sodium chloride. The chloroform layer was dried over magnesium sulfate and then filtered. The filtrate was concentrated under reduced pressure to give a reddish brown oily substance. The oily substance was purified by silica gel column chromatography (eluent, chloroform:methanol=150:1) to give 0.03 g of the isomer A of the desired 5-(α-propyl-3,4-dimethoxycinnamylidene)-4-oxo-2-thioxothiazolidine from the first eluate and 0.2 g of the isomer B from the subsequent eluate.

Isomer A

Red crystals, m.p. 185°–189° C.
Mass spectrum (m/e); 349(M+).
NMR(CDCl$_3$) δ(ppm): 1.10(t, 3H), 1.50–180(m, 2H), 3.00–3.20(m, 2H), 3.88(s, 3H), 3.90(s, 3H), 6.80(d, 1H, J=16 Hz), 6.80–7.20(m, 4H), 10.4(br.s, 1H).
IR(KBr) cm$^{-1}$: 1684, 1594, 955.

Isomer B

Red crystals, m.p. 192°–198° C.
Mass spectrum (m/e); 349 (M+).
NMR(CDCl$_3$) δ(ppm): 1.08(s, 3H), 1.50–1.80(m, 2H), 2.35–2.55(m, 2H), 3.90(s, 3H), 3.98(s, 3H), 6.80–7.20(m, 4H), 8.50(d, 1H, J=16 Hz), 10.2(br.s, 1H).
IR(KBr) cm$^{-1}$: 1669, 1595, 969.

EXAMPLE 9

5-(α-Propyl-3,4,5-trimethoxycinnamylidene)-4-oxo-2-thioxothiazolidine

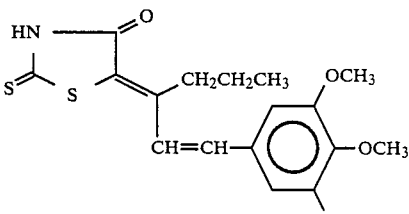

Following the same procedure as in Example 8 but substituting 1-(3,4,5-trimethoxyphenyl)-1-hexen-3-one for the ketone used therein, there were obtained 0.07 g of the isomer A and 0.20 g of the isomer B of the title compound.

Isomer A

Yellow crystals, m.p. 223°–226° C. (dec.).
Mass spectrum (m/e); 379 (M+).
NMR(CDCl$_3$) δ(ppm): 1.08(t, 3H), 1.50–1.75(m, 2H), 3.00–3.15(m, 2H), 3.90(s, 3H), 3.95(s, 6H), 6.55(d, 1H, J=16 Hz), 6.70(s, 2H), 7.10(d, 1H, J=16 Hz), 10.5(br.s, 1H).
IR(KBr) cm$^{-1}$: 1678, 1605, 1578, 949.

Isomer B

Red crystals, m.p. 193°–199° C. (dec.).
Mass spectrum (m/e); 379 (M+).
NMR(CDCl$_3$) δ(ppm): 1.05(t, 3H), 1.50–1.80(m, 2H), 2.40–2.60(m, 2H), 3.90(s, 3H), 3.95(s, 6H), 6.80(s, 2H), 7.00(d, 1H, J=16 Hz), 8.50(d, 1H, J=16 Hz), 10.3(br.s, 1H).
IR(KBr) cm$^{-1}$: 1675, 1604, 1578, 966.

EXAMPLE 10

5-[3-(2-Thienyl)-1-ethyl-2-propenylidene]-4-oxo-2-thioxothiazolidine

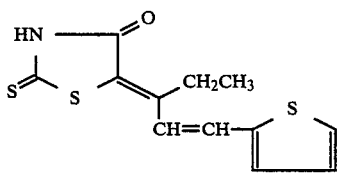

Following the same procedure as in Example 8 but substituting 1-(2-thienyl)-pentene-3-one for the ketone used therein, there was obtained 0.33 g of the title compound.

Red crystals, m.p. 212°–218° C. (dec.).
NMR(CDCl$_3$) δ(ppm): 1.24(t, 3H), 2.48(q, 2H), 7.00–7.10(m, 1H), 7.20–7.30(m, 2H), 7.37(d, 1H, J=16 Hz), 8.38(d, 1H, J=16 Hz), 9.60(br.s, 1H).
IR(KBr) cm$^{-1}$: 1675, 1589, 1547, 958.

EXAMPLE 11

5-[3-(2-Pyrrolyl)-1-methyl-2-propenylidene]-4-oxo-2-thioxothiazolidine

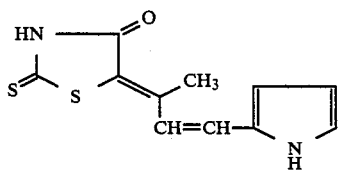

Following the same procedure as in Example 8 but substituting 4-(2-pyrrolyl)-3-butene-2-one for the ketone used therein, there was obtained 0.10 g of the title compound.

Brown crystals, m.p. 176°–180° C. (dec.).
Mass spectrum (m/e); 250 (M+).
NMR(DMSO-d$_6$) δ(ppm): 2.12(s, 3H), 6.15–6.22(m, 1H), 6.45–6.55(m, 1H), 6.95–7.05(m, 1H), 7.16(d, 1H, J=16 Hz), 8.14(d, 1H, J=16 Hz).
IR(Nujol) cm$^{-1}$: 1670, 1600, 1550, 960.

EXAMPLE 12

5-[3-(3,4-Dimethoxyphenyl)-1-methylpropylidene]-4-oxo-2-thioxothiazolidine

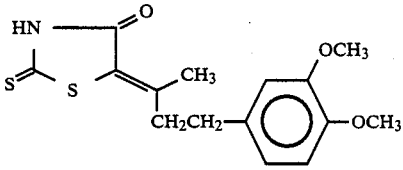

Following the same procedure as in Example 8 but substituting 4-(3,4-dimethoxyphenyl)-2-butanone for the ketone used therein, there were obtained 0.19 g of the isomer A and 0.18 g of the isomer B of the title compound.

Isomer A

Yellow crystals, m.p. 143.5°–145.5° C.
Mass spectrum (m/e); 323(M+).
NMR(CDCl$_3$) δ(ppm): 2.40(s, 3H), 2.47(t, 2H), 2.80(t, 2H), 3.86(s, 3H), 3.89(s, 3H), 6.65–6.85(m, 3H), 9.60(br.s, 1H).
IR(KBr) cm$^{-1}$: 1695, 1609, 1516, 976.

Isomer B

Yellow crystals, m.p. 156°–158° C.
Mass spectrum (m/e); 323 (M+).
NMR(CDCl$_3$) δ(ppm): 1.95(s, 3H), 2.78(t, 2H), 3.15(t, 2H), 3.86(s, 3H), 3.89(s, 3H), 6.80(s, 3H), 9.66(br.s, 1H).
IR(KBr) cm$^{-1}$: 1690, 1608, 1517, 969.

EXAMPLE 13

Ethyl 4-[3-(4-oxo-2-thioxo-5-thiazolidinylidene)-1-buten-1-yl]phenoxyacetate

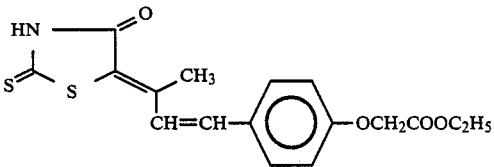

Following the same procedure as in Example 8 but substituting ethyl 4-(3-oxo-1-butenyl)phenoxyacetate for the ketone used therein, there were obtained 0.28 g of the isomer A and 0.32 g of the isomer B of the title compound.

Isomer A

Yellow crystals, m.p. 209°–213° C. (dec.).
Mass spectrum (m/e); 363 (M+).
NMR(DMSO-d$_6$) δ(ppm): 1.22(t, 3H), 2.50(s, 3H), 4.17(q, 2H), 4.80(s, 2H), 6.65(d, 1H, J=16 Hz), 6.95(d, 2H), 7.32(d, 1H, J=16 Hz), 7.68(d, 2H), 13.40(br.s, 1H).
IR(KBr) cm$^{-1}$: 1740, 1680, 1603, 970, 959.

Isomer B

Yellow crystals, m.p. 220°–223° C. (dec.).
Mass spectrum (m/e); 363 (M+).
NMR(DMSO-d$_6$) δ(ppm): 1.22(t, 3H), 2.16(s, 3H), 4.20(q, 2H), 4.80(s, 2H), 7.00(d, 2H), 7.28(d, 1H, J=16 Hz), 7.54(d, 2H), 8.45(d, 1H, J=16 Hz), 13,45(br.s, 1H).
IR(KBr) cm$^{-1}$: 1772, 1689, 1604, 981, 926.

EXAMPLE 14

Ethyl 6-(3,4-dimethoxyphenyl)-4-(4-oxo-2-thioxo-5-thiazolidinylidene)-5-hexenoate

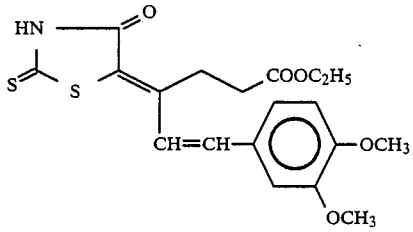

Following the same procedure as in Example 8 but substituting ethyl 6-(3,4-dimethoxyphenyl)-4-oxo-5-hexenoate for the ketone used therein, there was obtained 0.12 g of the title compound.

Reddish brown crystals, m.p. 178°–179.5° C.
NMR(CDCl$_3$) δ(ppm): 1.30(t, 3H), 2.50–2.65(m, 2H), 2.75–2.90(m, 2H), 3.92(s, 3H), 3.95(s, 3H), 4.18 (q, 2H), 6.80–7.20(m, 4H), 8.47(d, 1H, J=16 Hz), 9.75(br.s, 1H).
IR(KBr) cm$^{-1}$: 1730, 1671, 1540, 979.

EXAMPLE 15

5-[3-(2-Thienyl)-1-methyl-2-propenylidene]-4-oxo-2-thioxothiazolidine

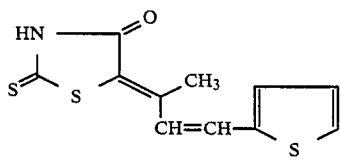

A mixture of 1.33 g (0.01 mol) of rhodanine, 1.52 g (0.01 mol) of 4-(2-thienyl)-3-butene-2-one, 0.15 g (0.002 mol) of ammonium acetate and 20 ml of toluene was heated under reflux for 24 hours. After cooling, the reaction mixture was purified by silica gel column chromatography (eluent, chloroform) to give 0.15 g of the isomer A of 5-[3-(2-thienyl)-1-methyl-1-methyl-2-propenylidene]-4-oxo-2-thioxothiazolidine from the first eluent and 0.08 g of the isomer B from the subsequent eluate.

Isomer A

Reddish brown crystals.
NMR(DMSO-d$_6$) δ(ppm): 2.14(s, 3H), 7.12(t, 1H), 7.34(d, 1H), 7.52(d, 1H, J=16 Hz), 7.64(d, 1H), 8.30(d, 1H, J=16 Hz).
IR(Nujol) cm$^{-1}$: 1650, 1580, 960.

Isomer B

Reddish brown crystals, m.p. 214°–217° C. (dec.).
NMR(DMSO-d$_6$) δ(ppm): 2.50(s, 3H), 6.45(d, 1H, J=16 Hz), 7.14(t, 1H), 7.48(d, 1H), 7.58(d, 1H, J=16 Hz), 7.70(d, 1H).
IR(Nujol) cm$^{-1}$: 1675, 1590, 940.

EXAMPLE 16

5-[3-(5-Chloro-2-thienyl)-1-methyl-2-propenylidene]-4-oxo-2-thioxothiazolidine

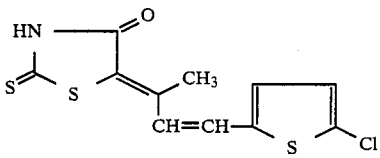

Following the same procedure as in Example 15 but substituting 4-(5-chloro-2-thienyl)-3-buten-2-one for the ketone used therein, there were obtained 0.20 g of the isomer A and 0.17 g of the isomer B of the title compound.

Isomer A

Reddish brown crystals, m.p. 237°–239° C. (dec.).
NMR(CDCl$_3$) δ(ppm): 2.14(s, 3H), 6.87(d, 1H), 7.02(d, 1H), 7.08(d, 1H, J=16 Hz), 8.30(d, 1H, J=16 Hz).
IR(Nujol) cm$^{-1}$: 1670, 1580, 1550, 970.

Isomer B

Yellow crystals, m.p. 250°–251° C. (dec.).
NMR(DMSO-d$_6$) δ(ppm): 2.50(s, 3H), 6.38(d, 1H, J=16 Hz), 7.16(d, 1H), 7.38(d, 1H), 7.49(d, 1H, J=16 Hz).
IR(Nujol) cm$^{-1}$: 1695, 1590, 1550, 940.

EXAMPLE 17

4-[3-(4-Oxo-2-thioxo-5-thiazolidinylidene)-1-hexen-1-yl]benzoic acid

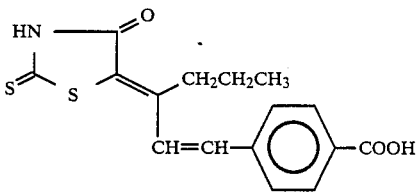

A mixture of 0.73 g (0.0055 mol) of rhodanine, 1.09 g (0.005mol) of 4-(3-oxo-hexen-1-yl)benzoic acid, 0.39 g (0.005 mol) of ammonium acetate and 10 ml of toluene was heated under reflux for 5 hours. After cooling, acetic acid was added to the reaction mixture and the precipitate was recovered by filtration. The precipitate was recrystallized from chloroform-methanol to give 0.10 g of the isomer A of the desired 4-[3-(4-oxo-2-thioxo-5-thiazolidinylidene)-1-hexen-1-yl]benzoic acid. To the filtrate was added water and the resulting mixture was extracted with chloroform (100 ml×3). The chloroform layer was washed three times with water and then once with a saturated aqueous solution of sodium chloride. The layer was dried over magnesium sulfate and then filtered. The filtrate was concentrated under reduced pressure and the residue was purified by silica gel column chromatography (eluent, chlorform : methanol=10:1) to give 0.10 g of the isomer B of the desired product.

Isomer A

Yellow crystals, m.p. 278°–280° C. (dec.).
Mass spectrum (m/e); 333(M$^+$).

NMR(DMSO-d₆) δ(ppm): 1.00(t, 3H), 1.45–1.70(m, 2H), 7.40(d, 1H, J=16 Hz), 7.70(d, 2H, J=8 Hz), 7.95(d, 2H, J=8 Hz), 8.58(d, 1H, J=16 Hz), 3.00(br.s, 1H), 3.60(br.s, 1H).
IR(KBr) cm⁻¹: 1695, 1680, 1605, 980.

Isomer B

Yellow crystals, m.p. 257°–261° C. (dec.).
Mass spectrum (m/e); 333(M⁺).
IR(KBr) cm⁻¹: 1690, 1605, 1540, 945.

EXAMPLE 18

3-[3-(4-Oxo-2-thioxo-5-thiazolidinylidene)-1-buten-1-yl]phenoxyacetic acid

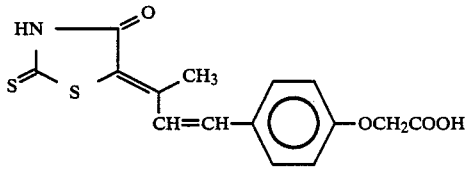

A mixture of 0.12 g of the isomer A of ethyl 4-[3-(4-oxo-2-thioxo-5-thiazolidinylidene)-1-buten-1-yl]phenoxyacetate prepared as described in Example 13, 5 ml of water and 1 ml of a 5% aqueous sodium hydroxide solution was stirred at room temperature for one hour. To the reaction mixture was added 10% hydrochloric acid to precipitate crystals. The crystals were recovered by filtration and washed with methanol to give 0.07 g of the isomer A of the desired 4-[3-(4-oxo-2-thioxo-5-thiazolidinylidene)-1-buten-1-yl]phenoxyacetic acid and also 0.07 g of the isomer B thereof.

Isomer A

Brown crystals, m.p. 260°–263° C. (dec.).
Mass spectrum (m/e); 335(M⁺).
NMR(DMSO-d₆) δ(ppm): 2.50(s, 3H), 4.70(s, 2H), 6.65(d, 1H, J=16 Hz), 6.95(d, 2H), 7.30(d, 1H, J=16 Hz), 7.65(d, 2H), 13.30(br.s, 1H).
IR(KBr) cm⁻¹: 1753, 1674, 1599, 958.

Isomer B

Brown crystals, m.p. 261°–263° C. (dec.).
Mass spectrum (m/e); 335(M⁺).
NMR(DMSO-d₆) δ(ppm): 2.15(s, 3H), 4.70(s, 2H), 7.00(d, 2H), 7.28(d, 1H, J=16 Hz), 7.54(d, 2H), 8.45(d, 1H, J=16 Hz), 13.40(br.s, 1H).
IR(KBr) cm⁻¹: 1740, 1699, 1603, 973.

EXAMPLE 19

7-(3,4-Dimethoxyphenyl)-5-(4-oxo-2-thioxo-5-thiazolidinylydene)-6-heptenoic acid

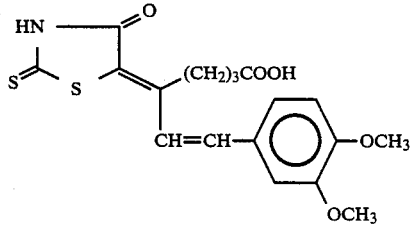

A mixture of 1.60 g (0.012 mol) of rhodanine, 3.06 g (0.01 mol) of ethyl 7-(3,4-dimethoxyphenyl)-5-oxo-6-heptenoate, 0.77 g (0.01 mol) of ammonium acetate and 20 ml of toluene was heated under reflux for 8 hours. After cooling, 100 ml of water added to the reaction mixture, which was then extracted with ethyl acetate (100 ml×3). The ethyl acetate layer was washed three times with water and once with a saturated aqueous solution of sodium chloride, and dried over magnesium sulfate and then filtered. The filtrate was concentrated under reduced pressure to give a reddish brown oily substance. The oily substance was purified by silica gel column chromatography (eluent, chloroform) to give 0.5 g of the desired ethyl 7-(3,4-dimethoxyphenyl)-5-(4-oxo-2-thioxo-5-thiazolidinilydene)-6-heptenoate. To 0.21 g of this compound were added 5 ml of water and 1 ml of a 5% aqueous sodium hydroxide solution and the mixture was stirred at room temperature for 3 hours. The reaction mixture was made acidic with 10% hydrochloric acid, mixed with 100 ml of water and then extracted with ethyl acetate (120 ml×3). The ethyl acetate layer was washed three times with water and once with a saturated aqueous solution of sodium chloride, dried over magnesium sulfate and then filtered. The filtrate was concentrated under reduced pressure and the residue was purified by silica gel column chromatography (eluent, chloroform:methanol=10:1) to give 0.12 g of the isomer A of the desired 7-(3,4-dimethoxyphenyl)-5-(4-oxo-2-thioxo-5-thiazolidinilydene)-6-heptenoic acid from the first eluate and 0.03 g of the isomer B thereof from the subsequent eluate.

Ethyl Ester of the Title Compound

Reddish brown crystals, m.p. 146°–148° C. (dec.).
Mass spectrum (m/e); 421 (M⁺).
IR(KBr) cm⁻¹: 1714, 1671, 1596, 1577, 971.

Isomer A

Reddish brown crystals, m.p. 223°–225° C. (dec.).
Mass spectrum (m/e); 393 (M⁺).
NMR(DMSO-d₆) δ(ppm): 1.80–2.00(m, 2H), 2.40–2.50(m, 2H), 2.52–2.70(m, 2H), 3.91(s, 3H), 3.93(s, 3H), 6.89(d, 1H), 7.10–7.20(m, 3H), 8.01(d, 1H, J=16 Hz), 13.00(br.s, 1H).
IR(KBr) cm⁻¹: 1697, 1596, 1541, 972.

Isomer B

Reddish brown crystals, m.p. 178°–180° C. (dec.).
Mass spectrum (m/e); 393 (M⁺).
NMR(DMSO-d₆) δ(ppm): 1.80–2.00(m, 2H), 2.35–2.50(m, 2H), 3.05–3.25(m, 2H), 3.91(s, 3H), 3.93(s, 3H), 6.50(d, 1H, J=16 Hz), 6.80–6.95(m, 1H), 7.00–7.20(m, 2H), 7.28(d, 1H, J=16 Hz), 12.30(br.s, 1H).
IR(KBr) cm⁻¹: 1704, 1595, 1540, 954.

EXAMPLE 20

5-[α-Hexyl-4-(1H-tetrazol-5-yl)-methoxycinnamylidene]-4-oxo-2-thioxothiazolidine

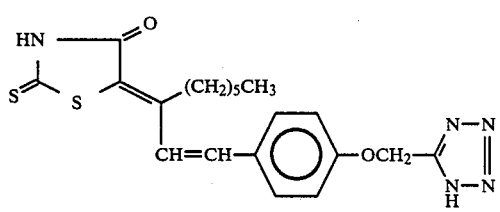

Following the same procedure as in Example 3 but substituting 1-[4-(tetrazol-5-yl-methyloxy)phenyl]-1-nonene-3-one for the ketone used therein, there was obtained 0.2 g of the title compound.

Brown crystals, m.p. over 300° C.

NMR (DMSO-d$_6$) δ(ppm): 0.80–1.00(m, 3H), 1.20–1.60(m, 8H), 2.35–2.50(m,2H), 5.24(s, 2H), 7.05–7.20(m, 3H), 7.50(d, 2H), 8.50(d, 1H, J=16 Hz).

IR(KBr) cm$^{-1}$: 3400, 1675, 1600, 1573, 970.

EXAMPLE 21

5-[3-(4-Hydroxy-3-methoxyphenyl)-1-methylpropylidene]-4-oxo-2-thioxothiazolidine

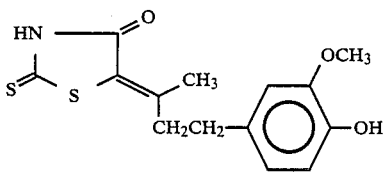

Following the same procedure as in Example 8 but substituting 4-(4-hydroxy-3-methoxyphenyl)-2-butanone for the ketone used therein, there was obtained 0.37 g of the title compound.

Yellow crystals, m.p. 182°–184° C. (dec.).

Mass spectrum (m/e); 309(M+).

NMR(CDCl$_3$) δ(ppm): 1.92(s, 3H), 2.73(t, 2H), 3.11(t, 2H), 3.87(s,3H), 6.60–6.83(m, 3H), 7.07(s, 1H), 12.70(br.s, 1H).

IR(KBr) cm$^{-1}$: 3530, 1690, 1605, 1520, 1020, 925.

EXAMPLE 22

5-[3-(4-Isopropyl-3-methoxyphenyl)-1-methylpropylidene]-4-oxo-2-thiazolidinilydene

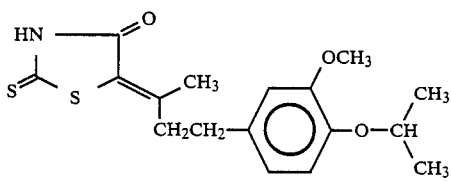

Following the same procedure as in Example 8 but substituting 4-(4-isopropoxy-3-methoxyphenyl)-2-butanone for the ketone used herein, there was obtained 0.47 g of the title compound.

Yellow crystals, m.p. 128°–130° C.

Mass spectrum (m/e); 351 (M+).

NMR(CDCl$_3$) δ(ppm): 1.35(d, 6H, J=6 Hz), 1.94(s, 3H), 2.76(t, 2H), 3.15(t, 2H), 3.85(s, 3H), 4.48(q, 1H, J=6 Hz), 6.71–6.84(m, 3H), 9.64(br.s, 1H).

IR(KBr) cm$^{-1}$: 3145, 1690, 1610, 1510, 1460, 1040, 960, 930.

EXAMPLE 23

5-[3-(3-Hydroxy-4-methoxyphenyl)-1-methylpropylidene]-4-oxo-2-thioxothiazolidine

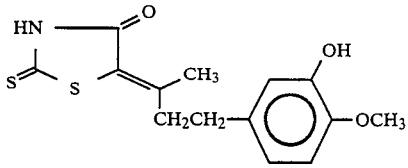

Following the same procedure as in Example 8 but substituting 4-(3-hydroxy-4-methoxyphenyl)-2-butanone for the ketone used therein, there was obtained 0.97 g of the title compound.

Yellow crystals, m.p. 188°–191° C. (dec.).

Mass spectrum (m/e); 309 (M+).

NMR(CDCl$_3$) δ(ppm): 1.90(s, 3H), 2.70(t, 2H), 3.09(t, 2H), 3.86(s, 3H), 6.65–6.83(m, 4H), 12.53(br.s, 1H).

IR(KBr) cm$^{-1}$: 3525, 1680, 1600, 1520, 1450, 1080, 980, 960.

EXAMPLE 24

5-[3-(3,5-Diisopropyl-4-hydroxyphenyl)-1-methylpropylidene]-4-oxo-2thioxothiazolidine

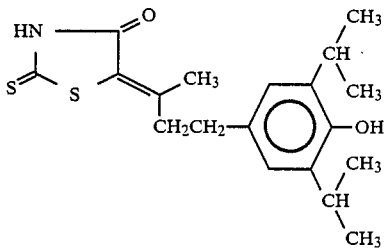

Following the same procedure as in Example 8 but substituting 4-(3,5-diisopropyl-4-hydroxyphenyl)-2-butanone for the ketone used therein, there was obtained 0.25 g of the isomer A and 0.35 g of the isomer B of the title compound.

Isomer A

Yellow crystals, m.p. 163°–166° C. (dec.).

NMR(CDCl$_3$) δ(ppm): 1.25(d, 12H, J=6 Hz), 1.90(s, 3H), 2.76(t, 2H), 3.00–3.20(m, 4H), 6.89(s, 2H), 9.40(br.s, 1H).

IR(KBr) cm$^{-1}$: 3505, 1690, 1610, 1455, 1080, 940.

Isomer B

Yellow crystals, m.p. 160°–163° C. (dec.).

NMR(CDCl$_3$) δ(ppm): 1.25(d, 12H, J=6 Hz), 2.41(s, 3H), 2.46(t, 2H), 2.78(t, 2H), 3.13(q, 2H, J=6 Hz), 4.80(br.s, 1H), 6.82(s, 2H), 9.30(br.s, 1H).

IR(KBr) cm$^{-1}$: 3440, 1700, 1610, 1425, 1070, 940.

EXAMPLE 25

Inhibitory Activity On Leukotrienes

The compounds were evaluated for inhibitory activity on leukotrienes in the following test.

In this test, contraction was induced in excised bronchi of guinea pigs by the action of leukotriene D$_4$, and inhibitory action of the present compounds after treatment before 10 minutes was measured and recorded via a transducer. The results are shown in Table 1.

TABLE 1

| Compound Tested | Percent Inhibition (%) (Conc. $10^{-5}$ M) |
|---|---|
| Isomer B of Example 1 | 82.4 |
| Compound of Example 14 | 98.1 |
| Isomer B of Example 19 | 85.1 |
| Ethyl ester compound of Example 19 | 90.5 |
| Isomer A of Example 17 | 84.7 |
| Isomer B of Example 17 | 79.8 |
| Isomer B of Example 12 | 97.9 |
| Isomer A of Example 12 | 100.0 |

EXAMPLE 26

Inhibitory Activity On Biosynthesis And Release Of Chemical Mediator

The compounds were evaluated for inhibitory activity on biosynthesis and release of a chemical mediator according to the method described by S. Watanabe-Kohno et al [J. Immunol., 125, 946 (1980)] and J. Augastein et al [Nature, 245, 215 (1973)]. In this test, SRS-A was used as a chemical mediator.

The chemical mediator contained in the reaction solution was determined according to bioassay using excised ileum of guinea pigs.

Percent Inhibition (%) = $(1 - A'/A) \times 100$

A' = contraction level by the reaction solution treated with test compound
A = contraction level by the control reaction solution

| Compound Tested | Percent Inhibition (%) (Conc. $10^{-5}$ M) |
|---|---|
| Isomer B of Example 1 | 58.0 |
| Isomer A of Example 12 | 76.2 |
| Isomer B of Example 12 | 70.6 |

The results of Examples 25 and 26 show that the compounds of the invention are of an inhibitory activity on leukotrienes and an inhibitory activity on biosynthesis and release of a chemical mediator.

The compounds (Isomer B of Example 1, Isomers A and B of Example 12, the compound of Example 14 and Isomer B of Example 15) demonstrate an inhibitory activity of 60–90% at a concentration of $10^{-5}$M on contraction of excised bronchi of guinea pigs by histamine and $PGF_{2\alpha}$.

The compounds of the invention generally show a lower toxicity to rats; for instance, no mortality was observed at 1000 mg/kg by oral administration with regard to Isomers A and B of Example 12.

| Pharmaceutical Example 1 | |
|---|---|
| Tablets (one tablet) | |
| 5-(α-Methyl-3,4-dimethoxycinnamylidene)-4-oxo-2-thioxothiazolidine (active ingredient) | 10 mg |
| Lactose | 67 mg |
| Crystalline cellulose | 15 mg |
| Cornstarch | 7 mg |
| Magnesium stearate | 1 mg |
| | 100 mg |

The above components were uniformly blended to form a powder for direct tabletting. The powder was compressed on a rotary tablet machine to yield tablets each weighing 100 mg and having a diameter of 6 mm.

| Pharmaceutical Example 2 | |
|---|---|
| Granules (one divided form) | |
| 5-(α-Methyl-3,4-dimethoxycinnamylidene)-4-oxo-2-thioxothiazolidine (active ingredient) | 10 mg |
| Lactose | 90 mg |
| Cornstarch | 50 mg |
| Crystalline cellulose | 50 mg |
| Hydroxypropylcellulose | 10 mg |
| Ethanol | 90 mg |

The active ingredient, lactose, cornstarch and cellulose were uniformly blended and a solution of hydroxypropylcellulose in ethanol was added. The resulting mixture was kneaded and granulated according to extrusion granulation method and the granules were dried in a dryer at 50° C. The dried granules were sieved out to a grain size of 297 μm–1460 μm to form granules. One divided form contains 200 mg.

| Pharmaceutical Example 3 | |
|---|---|
| Syrups | |
| 5-(α-Methyl-3,4-dimethoxycinnamylidene)-4-oxo-2-thioxothiazolidine (active ingredient) | 1.000 g |
| Refined sugar | 30.000 g |
| D-Sorbitol, 70 w/v % | 25.000 g |
| Ethyl paraoxybenzoate | 0.030 g |
| Propyl paraoxybenzoate | 0.015 g |
| Flavoring agent | 0.200 g |
| Glycerol | 0.150 g |
| 96% Ethanol | 0.500 g |
| Distilled water | ad lib. |
| Total | 100 ml |

In 60 g of hot water were dissolved refined sugar, D-sorbitol, ethyl paraoxybenzoate, propyl paraoxybenzoate and the active ingredient. After cooling, a solution of flavoring agent dissolved in glycerol and ethanol was added. Then, water was added to the mixture to make up to 100 ml.

| Pharmaceutical Example 4 | |
|---|---|
| Injectable solutions | |
| 5-(α-Methyl-3,4-dimethoxycinnamylidene)-4-oxo-2-thioxothiazolidine (active ingredient) | 1 mg |
| Sodium chloride | 10 mg |
| Distilled water | ad lib. |
| Total | 1.0 ml |

Sodium chloride and the active ingredient were dissolved in distilled water to make up a total to 1.0 ml.

| Pharmaceutical Example 5 |
|---|
| Suppositories |

-continued

Pharmaceutical Example 5

| | |
|---|---|
| 5-(α-Methyl-3,4-dimethoxycinnamylidene)-4-oxo-2-thioxothiazolidine (active ingredient) | 2 g |
| Polyethylene glycol 4000 | 20 g |
| Glycerol | 78 g |
| Total | 100 g |

Glycerol was added to the active ingredient and then polyethylene glycol 4000 was added. The mixture was molten with heating and injected into a suppository dio and solidified by cooling to prepare suppositories, each weighing 1.5 g.

Pharmaceutical Example 6

| Inhalations | |
|---|---|
| 5-(α-Methyl-3,4-dimethoxycinnamylidene)-4-oxo-2-thioxothiazolidine (active ingredient) | 0.1 g |
| Sodium chloride | 1.0 g |
| Glycerol | 1.0 g |
| Distilled water | ad lib. |
| Total | 100 ml |

Sodium chloride, glycerol and the active ingredient were dissolved in distilled water to make up a total to 100 ml.

As explained above in detail, the compounds of formula (I) and pharmaceutically acceptable salts thereof have a potent inhibitory activity on chemical mediators including leukotrienes and are thus useful for the prophylaxis and treatment of allergic diseases, e.g., bronchial asthma, allergic rhinitis, urticaria, isochemic heart diseases, arteriosclerosis, psoriasis and inflammations.

What is claimed is:

1. A rhodanine derivative of Formula (I)

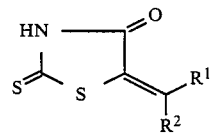
(I)

wherein $R^1$ is $C_1$-$C_6$ alkyl, a group —$(CH_2)_n COOR^3$ in which n is an integer of 1 to 4 and $R^3$ is hydrogen or $C_1$-$C_6$ alkyl, and $R^2$ is a group —CH=CH—$R^4$ wherein $R^4$ is phenyl or substituted phenyl having one or more substituents selected from $C_1$-$C_6$ alkyl, $C_1$-$C_6$ alkoxy, hydroxyl, halogen, carboxyl, and carboxyl-, alkoxycarbonyl— or tetrazolyl—substituted alkoxy, thienyl, halogen—substituted thienyl or pyrrolyl, or $R^2$ is a group —$CH_2$—$CH_2$—$R^4$ wherein $R^4$ is phenyl optionally substituted by $C_1$-$C_6$ alkyl, $C_1$-$C_6$ alkoxy or hydroxyl or a pharmaceutically acceptable salt thereof.

2. A pharmaceutical composition having a chemical transmitter inhibitory activity, which comprisesas an active ingredient a rhodanine derivative of Formula (I)

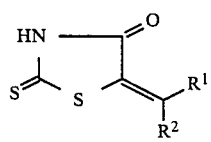
(I)

wherein $R^1$ is $C_1$-$C_6$ alkyl, a group —$(CH_2)_n COOR^3$ in which n is an integer of 1 to 4 and $R^3$ is hydrogen or $C_1$-$C_6$ alkyl, and $R^2$ is a group —CH=CH—$R^4$ wherein $R^4$ is phenyl or substituted phenyl having one or more substituents selected from $C_1$-$C_6$ alkyl, $C_1$-$C_6$ alkoxy, hydroxyl, halogen, carboxyl, and carboxyl-, alkoxycarbonyl—or tetrazolyl—substituted alkoxy, thienyl, halogen—substituted thienyl or pyrrolyl, or $R^2$ is a group —$CH_2$—$CH_2$—$R^4$ wherein $R^4$ is phenyl optionally substituted by $C_1$-$C_6$ alkyl, $C_1$-$C_6$ alkoxy or hydroxyl or a pharmaceutically acceptable salt thereof associated with one or more pharmaceutically acceptable additives or excipients therefor.

* * * * *